(12) United States Patent
Najarian et al.

(10) Patent No.: US 8,536,138 B2
(45) Date of Patent: *Sep. 17, 2013

(54) TREATMENT OF PULMONARY HYPERTENSION WITH CARBONIC ANHYDRASE INHIBITORS

(75) Inventors: Thomas Najarian, Los Osos, CA (US); Peter Y. Tam, Redwood City, CA (US); Leland F. Wilson, Menlo Park, CA (US); Craig Peterson, Mountain View, CA (US)

(73) Assignee: Vivus, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,476

(22) Filed: Dec. 5, 2011

(65) Prior Publication Data

US 2012/0196881 A1 Aug. 2, 2012

Related U.S. Application Data

(63) Continuation of application No. 11/818,306, filed on Jun. 13, 2007, now Pat. No. 8,071,557.

(51) Int. Cl.
| | | |
|---|---|---|
| *A61K 31/53* | (2006.01) | |
| *A61K 31/407* | (2006.01) | |
| *A61K 31/506* | (2006.01) | |
| *A61K 31/513* | (2006.01) | |
| *A61K 31/519* | (2006.01) | |
| *A61K 31/7048* | (2006.01) | |
| *A61P 11/00* | (2006.01) | |
| *A61K 31/137* | (2006.01) | |

(52) U.S. Cl.
USPC .......... 514/23; 514/243; 514/250; 514/261.1; 514/269; 514/275

(58) Field of Classification Search
None
See application file for complete search history.

(56) References Cited

U.S. PATENT DOCUMENTS

| | | | |
|---|---|---|---|
| 5,242,391 A | 9/1993 | Place et al. | |
| 5,474,535 A | 12/1995 | Place et al. | |
| 5,773,020 A | 6/1998 | Place et al. | |
| 6,656,935 B2 | 12/2003 | Yamada et al. | |
| 2003/0144347 A1* | 7/2003 | Ryback | 514/459 |
| 2004/0005358 A1 | 1/2004 | Slugg et al. | |

FOREIGN PATENT DOCUMENTS

| | | |
|---|---|---|
| WO | WO-0076493 A1 | 12/2000 |
| WO | WO-2005089766 A1 | 9/2005 |
| WO | WO-2006063078 A2 | 6/2006 |
| WO | WO-2007084290 A2 | 7/2007 |
| WO | WO-2008060963 A2 | 5/2008 |

OTHER PUBLICATIONS

Galie, N. et al "Sildenafil citrate therapy for pulmonary . . . " NEJM (2005) vol. 353, No. 20, pp. 2148-2157.*
Roisenblatt, S. et al "A double-blind, placebo-controlled, crossover . . . " Arch. Intern. Med. (2006) vol. 166, pp. 1763-1767.*
Sabroe, I. et al "Practical and conceptual models of chronic obstructive . . . " Proc. Am. Thorac. Soc. (2007) vol. 4, pp. 606-610.*
Affuso et al. "Tadalafil Improves Quality of Life and Exercise Tolerance in Idiopathic Pulmonary Arterial Hypertension." *Int. J. Cardiol.* 108.3(2006):429-431.
Barberá et al. "Pulmonary Hypertensionin Chronic Obstructive Pulmonary Disease." *Eur. Respir. J.* 21.5(2003):892-905.
Humpl et al. "Beneficial Effect of Oral Sildenafil Therapy on Childhood Pulmonary Arterial Hypertension: Twelve-Month Clinical Trial of a Single-Drug, Open-Label, Pilot Study." *Circulation.* 111(2005):3274-3280.
Höhne et al. "Pulmonary Vasodilation by Acetazolamide During Hypoxia is Unrelated to Carbonic Anhydrase Inhibition." *Am. J. Physiol. Lung Cell. Mol. Physiol.* 282.1(2007):L178-L184.
Lahav et al. "Intermittent Administration of Furosemide Vs Continuous Infusion Preceded by a Loading Dose for Congestive Heart Failure." *Chest J.* 102.3(1992):725-731.
Moraes et al. "Secondary Pulmonary Hypertension in Chronic Heart Failure: The Role of the Endothelium in Pathophysiology and Management." *Circulation.* 102.14(2000):1718-1723.
Nieminen et al. "Execute Summary of the Guidelines on the Diagnosis and Treatment of Acute Heart Failure: The Task Force on Acute Heart Failure of the European Society of Cardiology." *Eur. Heart J.* 26.4(2005):384-416.
Olson et al. "The Obesity Hypoventilation Syndrome." *Am. J. Med.* 118.9(2005):948-956.
Runo et al. "Primary Pulmonary Hypertension." *Lancet.* 361. 9368(2003):1533-1544.
Weber. "Topiramate for Obstructive Sleep Apnea and Snoring." *Am. J. Psychiatry.* 159.5(2002):872-873.

* cited by examiner

*Primary Examiner* — Leigh Maier

(74) *Attorney, Agent, or Firm* — Mintz, Levin, Cohn, Ferris, Glovsky and Popeo, P.C.; Ivor R. Elrifi; Matthew Pavao

(57) ABSTRACT

This disclosure relates generally to methods and pharmaceutical compositions useful in treating pulmonary hypertension. In one embodiment, for example, the disclosure provides a method for treating pulmonary hypertension comprising administering a therapeutically effective dose of a carbonic anhydrase inhibitor to a patient in need of treatment. The disclosure finds utility in the fields of medicine and pharmacology.

33 Claims, No Drawings

TREATMENT OF PULMONARY HYPERTENSION WITH CARBONIC ANHYDRASE INHIBITORS

RELATED APPLICATIONS

This application is a continuation of U.S. patent application Ser. No. 11/818,306, filed Jun. 13, 2007, the contents of which are incorporated herein.

TECHNICAL FIELD

This disclosure relates generally to methods and pharmaceutical compositions useful in treating pulmonary hypertension. The disclosure finds utility in the fields of medicine and pharmacology.

BACKGROUND

Pulmonary hypertension (PH), also known as pulmonary arterial hypertension (PAH), is a disorder characterized by high blood pressure in the arteries that supply the lungs. Pulmonary hypertension is often classified as either secondary pulmonary hypertension (SPH), in which the cause of the elevated blood pressure is known, or primary pulmonary hypertension (PPH), in which the cause is unknown. Examples of pre-existing conditions that may cause SPH include chronic obstructive pulmonary disease (COPD), sleep apnea, emphysema, bronchitis, sclerodema, CREST syndrome, systemic lupus erythematosus, chronic pulmonary thromboembolism, HIV infection, liver disease, and certain congenital heart diseases. Certain diet drugs such as fenfluramine and dexfenfluramine may also cause SPH.

In addition to high arterial blood pressure, PH may also be characterized by: narrowing and/or stiffening of the pulmonary arteries as the muscles within the walls of the arteries tighten or thicken; the formation of scar tissue in the walls of the pulmonary arteries; and the formation of blood clots within the smaller pulmonary arteries.

Symptoms of pulmonary hypertension include shortness of breath with minimal exertion, fatigue, chest pain, dizzy spells, low blood pressure, and fainting. The blood pressure in the pulmonary arteries of a patient suffering from PH may be twice as high or higher than the pulmonary blood pressure in a normal, healthy individual.

Although PPH is extremely rare, occurring in about two persons per million population per year, SPH is far more common and represents a significant medical concern for the population as a whole. Pulmonary hypertension is frequently misdiagnosed and progresses to late stage before it is accurately diagnosed.

There is no known cure for PH; current methods of treatment focus on prolonging patient lifespan and enhancing patient quality of life. Current methods of treatment of PH include administration of: vasodilators such as prostacyclin, epoprostenol, and sildenafil; endothelin receptor antagonists such as bosentan; calcium channel blockers such as amlodipine, diltiazem, and nifedipine; anticoagulants such as warfarin; and diuretics. Treatment of PH has also been carried out using oxygen therapy; and lung and/or heart transplantation. Each of these methods, however, suffers from one or multiple drawbacks which may include lack of effectiveness, serious side effects, low patient compliance, and high cost.

An ideal method of treatment would eliminate or significantly reduce the symptoms of PH, would lower pulmonary pressures, would be substantially more effective and easy to administer, and would have minimal or no side effects. The present disclosure is directed at providing one or more of these characteristics in a chemotherapeutic method for treating PH.

SUMMARY OF THE DISCLOSURE

The present disclosure describes compositions and methods for treating pulmonary hypertension.

In one embodiment, then, the present disclosure describes a method for treating pulmonary hypertension in a patient. The method comprises administering a therapeutically effective dose of a carbonic anhydrase inhibitor to the patient.

In another embodiment, the present disclosure describes a method for treating pulmonary hypertension in a patient. The method comprises administering to the subject a daily dose of a carbonic anhydrase inhibitor that is gradually increased, over an extended time period, from an initial daily dosage up to a final daily dosage suitable for continued maintenance therapy. The final daily dosage is in the range of about 10 mg to 400 mg.

In another embodiment, the present disclosure describes a pharmaceutical formulation comprising a therapeutically effective amount of a carbonic anhydrase inhibitor. The pharmaceutical formulation further comprises at least one additional active agent selected from a Type V phosphodiesterase inhibitor and an endothelin antagonist.

DETAILED DESCRIPTION OF THE INVENTION

Definitions and Nomenclature:

Before describing the present invention in detail, it is to be understood that unless otherwise indicated, this invention is not limited to particular formulations, active and inactive agents, modes of administration, or methods of treatment or use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like. Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

When referring to an active agent, applicants intend the term "active agent" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a patient as described herein encompasses prevention of pulmonary hypertension in a susceptible individual as well as treatment of a clinically symptomatic individual by inhibiting or causing regression of disease.

By the terms "effective amount" and "therapeutically effective amount" of a compound of the invention is meant a nontoxic but sufficient amount of the drug or agent to provide the desired effect.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient, provides a measurable time delay before drug is released from the formulation into the patient's body.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Active Agents, Dosages, and Formulations:

The invention involves administration of a carbonic anhydrase inhibitor to a patient afflicted with pulmonary hypertension, generally secondary pulmonary hypertension. Carbonic anhydrase inhibitors are generally imidazoles (such as imidazole per se), imidazole derivatives, sulfonamides (such as topiramate), and sulfonylureas (such as zonisamide). Any carbonic anhydrase inhibitor may be advantageously employed in conjunction with the present invention. Examples of suitable carbonic anhydrase inhibitors include, without limitation, acetazolamide (Diamox™), brinzolamide, diclofenamide, dichlorphenamide (Daranide™), dorzolamide, furosemide, imidazole, methazolamide (Neptazane™), phenylalanine, topiramate, and zonisamide. Carbonic anhydrase inhibitors also include selective inhibitors of the cyclooxygenase-2 enzyme ("cox 2 inhibitors"), such as such as celecoxib, valdecoxib, rofecoxib, etoricoxib, and the like. Preferred carbonic anhydrase inhibitors for use in conjunction with the present invention include, without limitation, acetazolamide, brinzolamide, diclofenamide, dichlorphenamide, dorzolamide, furosemide, imidazole, methazolamide, phenylalanine, topiramate, zonisamide, celecoxib, valdecoxib, rofecoxib, and etoricoxib, with acetazolamide, zonisamide, and topiramate particularly preferred. The oral daily dose of topiramate effective to treat pulmonary hypertension according to the method of the invention is generally in the range of about 10 mg to about 400 mg, preferably in the range of about 50 mg to about 250 mg, and optimally in the range of about 75 mg to about 225 mg. The daily dose may be undivided, such that carbonic anhydrase inhibitor is administered once a day, or the daily dose may be divided into two to four individual doses. Preferably, the topiramate is administered in sustained release form, as will be discussed infra, either once or twice daily to achieve a daily dosage in the aforementioned ranges. It will be appreciated that the daily dose of topiramate as well as other carbonic anhydrase inhibitors normally represents on the order of 25% to 200%, more generally 25% to 100%, and most typically 25% to 75%, of the daily dose known and/or prescribed for previously known indication(s) (as set forth, for example, in the Physicians' Desk Reference), using the same mode of administration.

In a preferred embodiment, the dosage of the carbonic anhydrase inhibitor is increased gradually at the outset of therapy, generally over a period of about three to ten weeks, more usually over a period of about three to about eight weeks, starting with a relatively low initial dose (on the order of 10 mg to 40 mg topiramate, preferably 15 mg to 35 mg topiramate, for instance), in order to reduce the likelihood of undesirable side effects. With topiramate, for example, a representative dosage regimen is as follows: administration of about 25 mg daily for about the first 5-7 days of treatment; administration of about 50 mg daily for the next 5-7 days; administration of about 75 mg daily for about the next 5-7 days; administration of about 100 mg daily for the next 5-7 days; and, subsequently, ongoing administration of a daily maintenance dose in the ranges specified earlier herein.

Administration of the active agent may be carried out using any appropriate mode of administration. Thus, administration can be, for example, oral, parenteral, transdermal, transmucosal (including rectal, vaginal, and transurethral), sublingual, by inhalation, or via an implanted reservoir in a dosage form. The term "parenteral" as used herein is intended to include subcutaneous, intravenous, and intramuscular injection.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy* (Easton, Pa.: Mack Publishing Co., 1995). For those compounds that are orally active, oral dosage forms are generally preferred, and include tablets, capsules, caplets, solutions, suspensions and syrups, and may also comprise a plurality of granules, beads, powders, or pellets that may or may not be encapsulated. Preferred oral dosage forms are tablets and capsules.

As noted above, it is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of the carbonic anhydrase inhibitor, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms for those carbonic anhydrase inhibitors that are orally active, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited earlier herein, which describes materials and methods for preparing encapsulated pharmaceuticals.

Oral dosage forms, whether tablets, capsules, caplets, or particulates, may, if desired, be formulated so as to provide for controlled release of the carbonic anhydrase inhibitor, and in a preferred embodiment, the present formulations are controlled release oral dosage forms. Generally, the dosage forms provide for sustained release, i.e., gradual, release of the carbonic anhydrase inhibitor from the dosage form to the patient's body over an extended time period, typically providing for a substantially constant blood level of the agent over a time period in the range of about 4 to about 12 hours, typically in the range of about 6 to about 10 hours. In a particularly preferred embodiment, there is a very gradual increase in blood level of the drug following oral administration of the dosage form containing the carbonic anhydrase inhibitor, such that peak blood level (generally about 50-200 µg/ml for topiramate, about 1-5 µg/ml for zonisamide, or about 10-35 µg/ml for acetazolamide), is not reached until at least 4-6 hours have elapsed, with the rate of increase of blood level drug approximately linear. In addition, in the preferred embodiment, there is an equally gradual decrease in blood level at the end of the sustained release period.

Generally, as will be appreciated by those of ordinary skill in the art, sustained release dosage forms are formulated by dispersing the active agent within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preferred sustained release dosage forms herein are composed of the acrylate and methacrylate copolymers available under the tradename "Eudragit" from Rohm Pharma (Germany). The Eudragit series E, L, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics. Other preferred Eudragit polymers are cationic, such as the Eudragit E, RS, and RL series polymers. Eudragit E100 and E PO are cationic copolymers of dimethylaminoethyl methacrylate and neutral methacrylates (e.g., methyl methacrylate), while Eudragit RS and Eudragit RL polymers are analogous polymers, composed of neutral methacrylic acid esters and a small proportion of trimethylammonioethyl methacrylate.

A particularly preferred dosage form according to the invention contains in the range of about 10 mg to about 400 mg topiramate, preferably in the range of about 50 to about 250 mg topiramate, most preferably in the range of about 75 mg to about 225 mg topiramate, and is formulated using Eudragit RS, Eudragit RL, or a blend of Eudragit RS and Eudragit RL, to provide sustained release over a time period in the range of about 4 to about 12 hours, typically in the range of about 6 to about 10 hours, following oral administration of the dosage form to a patient. Such formulations can be made using conventional means known to those of ordinary skill in the art, for example by coating active agent particles with the sustained release polymer(s) and either loading the coated particles into a capsule or compressing the coated particles into a tablet using tabletting excipients and a tablet press.

Preparations according to this invention for parenteral administration include sterile aqueous and nonaqueous solutions, suspensions, and emulsions. Injectable aqueous solutions contain the active agent in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

The active agent may also be administered through the skin using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agent may be formulated as a depot preparation for controlled release of the active agent, preferably sustained release over an extended time period. These sustained release dosage forms are generally administered by implantation (e.g., subcutaneously or intramuscularly or by intramuscular injection).

Although the present compositions will generally be administered orally, parenterally, transdermally, or via an implanted depot, other modes of administration are suitable as well. For example, administration may be transmucosal, e.g., rectal or vaginal, preferably using a suppository that contains, in addition to the active agent, excipients such as a suppository wax. Transmucosal administration also encompasses transurethral administration, as described, for example, in U.S. Pat. Nos. 5,242,391, 5,474,535, and 5,773,020 to Place et al. Formulations for nasal or sublingual administration are also prepared with standard excipients well known in the art. The pharmaceutical compositions of the invention may also be formulated for inhalation, e.g., as a solution in saline, as a dry powder, or as an aerosol.

In another embodiment of the invention, the method of treating the patient involves administering at least one additional active agent, i.e., in addition to the carbonic anhydrase inhibitor. The additional active agent may be, for example, a sympathomimetic amine, a Type V phosphodiesterase inhibitor, and/or an endothelin antagonist. In some cases, the additional active agent will reduce the quantity of the carbonic anhydrase inhibitor needed to achieve a therapeutic effect, e.g., a sympathomimetic amine such as phentermine or bupropion can reduce the minimum effective amount of a carbonic anhydrase inhibitor such as topiramate, zonisamide, or acetazolamide.

Sympathomimetic amines, including the catecholamines, are amine drugs that mimic the actions of drugs that activate the sympathetic nervous system, such as epinephrine and norepinephrine. Sympathomimetic amines thus include amphetamine, benzphetamine, bupropion, chlorphentermine, colterol, diethylpropion, dopamine, dobutamine, ephedrine, epinephrine, epinine, ethylnorepinephrine, fenfluramine, fenoldapam, hydroxyamphetamine, ibopamine, isoetharine, isoproterenol, mephentermine, metaproterenol, metaraminol, methoxamine, methoxyphenamine, midodrine, norepinephrine, phendimetrazine, phenmetrazine, phentermine, phenylephrine, phenylethylamine, phenylpropanolamine, prenalterol, propylhexedrine, protokylol, ritodrine, terbutaline, tuaminoheptane, tyramine, and acid addition salts thereof, either organic or inorganic. Common acid addition salts of some of the aforementioned sympathomimetic amines include, without limitation, dobutamine hydrochloride, epinephrine bitartrate, ethylnorepinephrine hydrochloride, fenoldapam mesylate, hydroxyamphetamine hydrobromide, isoproterenol hydrochloride, mephentermine sulfate, metaraminol bitartrate, methoxamine hydrochloride, norepinephrine bitartrate, phenylephrine hydrochloride, and terbutaline sulfate.

Preferably, the sympathomimetic amine is phentermine, chlorphentermine, or bupropion, with phentermine and bupropion particularly preferred. In an exemplary embodiment, the carbonic anhydrase inhibitor administered is topiramate and the sympathomimetic amine administered is phentermine, wherein the daily dose of topiramate is as given above for the monotherapeutic regimen, and the corresponding daily dose of phentermine that is co-administered is such that the weight ratio of the daily dose of topiramate to the daily dose of phentermine is in the range of about 2.5:1 to about 20:1, typically in the range of about 5:1 to about 20:1. In another exemplary embodiment, the carbonic anhydrase inhibitor administered is topiramate and the sympathomimetic amine administered is bupropion, wherein the daily dose of topiramate is as given above for the monotherapeutic regimen, and the corresponding daily dose of bupropion that is co-administered is such that the weight ratio of the daily dose of topiramate to the daily dose of bupropion is in the range of about 1:5 to about 3:1, preferably in the range of about 1:4 to about 2:1, most preferably in the range of about 1:4 to about 1.5:1

When the method of the invention involves combination therapy, i.e., wherein a secondary agent such as a sympathomimetic amine is co-administered with a carbonic anhydrase inhibitor, the agents may be administered separately, at the same or at different times of the day, or they may be administered in a single composition. In the former case, it is generally preferred that the sympathomimetic amine be administered later in the day than the carbonic anhydrase inhibitor, particularly when the amine drug acts as a CNS stimulant and could interfere with sleep. In the latter case, each agent can be administered in an "immediate release" manner or in a "controlled release manner." When the additional active agent is a sympathomimetic amine, for instance, any dosage form containing both active agents, i.e., both the carbonic anhydrase inhibitor and the sympathomimetic amine, can provide for immediate release or controlled release of the sympathomimetic amine, and either immediate release or controlled release of the carbonic anhydrase inhibitor. It is preferred, however, that the carbonic anhydrase inhibitor be in controlled release form, as described supra with respect to carbonic anhydrase inhibitor monotherapy. As an example, a combination dosage form of the invention for once-daily administration might contain in the range of about 50 mg to about 400 mg topiramate, preferably about 50 mg to about 250 mg topiramate, and optimally about 50 mg to about 150 mg topiramate, in controlled release (e.g., sustained release) form, and either phentermine in immediate release form, or bupropion in controlled release form, with the additional active agent present in an amount that provides a weight ratio of topiramate to phentermine, or a weight ratio of topiramate to bupropion, specified as above. In other formulations of the invention, two or more additional active agents, which may or may not be in the same class of drug (e.g., sympathomimetic amines), can be present in combination, along with the carbonic anhydrase inhibitor. In such a case, the effective amount of either or each individual additional active agent present will generally be reduced relative to the amount that would be required if only a single added agent were used. Specific examples of such once-daily formulations include the following:

(1) 200 mg topiramate, 15 mg phentermine;
(2) 200 mg topiramate, 10 mg phentermine;
(3) 150 mg topiramate, 15 mg phentermine;
(4) 150 mg topiramate, 10 mg phentermine;
(5) 100 mg topiramate, 15 mg phentermine;
(6) 100 mg topiramate, 10 mg phentermine;
(7) 200 mg topiramate, 300 mg bupropion;
(8) 200 mg topiramate, 250 mg bupropion;
(9) 200 mg topiramate, 200 mg bupropion;
(10) 200 mg topiramate, 150 mg bupropion;
(11) 200 mg topiramate, 100 mg bupropion;
(12) 100 mg topiramate, 300 mg bupropion;
(13) 100 mg topiramate, 250 mg bupropion;
(14) 100 mg topiramate, 200 mg bupropion;
(15) 100 mg topiramate, 150 mg bupropion;
(16) 100 mg topiramate, 100 mg bupropion;
(17) 200 mg topiramate, 300 mg bupropion, 5 mg phentermine;
(18) 150 mg topiramate, 300 mg bupropion, 5 mg phentermine;
(19) 100 mg topiramate, 300 mg bupropion, 5 mg phentermine;
(20) 200 mg topiramate, 250 mg bupropion, 10 mg phentermine;
(21) 150 mg topiramate, 250 mg bupropion, 10 mg phentermine; and
(22) 100 mg topiramate, 250 mg bupropion, 10 mg phentermine.

As may be deduced from the foregoing, representative topiramate/phentermine formulations typically contain 100 mg to 200 mg topiramate and: 100 mg to 300 mg bupropion; 10 mg to 15 mg phentermine; or 100 mg to 300 mg bupropion and 5 mg to 10 mg phentermine. The additional active agent may also be a Type V phosphodiesterase inhibitor, administered with the carbonic anhydrase inhibitor, or with both the carbonic anhydrase inhibitor and a sympathomimetic amine. Examples of Type V phosphodiesterase inhibitors include, without limitation, avanafil, sildenafil, tadalafil, zaprinast, dipyridamole, vardenafil and acid addition salts thereof. Avanafil, described in U.S. Pat. No. 6,656,935, is particularly preferred. In an exemplary embodiment, the carbonic anhydrase inhibitor administered is topiramate and the Type V phosphodiesterase inhibitor administered is avanafil, tadalafil, or sildenafil, wherein the daily dose of topiramate is as given above for the monotherapeutic regimen, and the corresponding daily dose of avanafil that is co-administered is such that the weight ratio of topiramate to avanafil is in the range of about 3:1 to about 1:3, typically in the range of about 2:1 to about 1:2. For sildenafil, which is approximately twice as potent as avanafil, the corresponding daily dose co-administered with topiramate is in the range of about 6:1 to about 1:1.5, typically about 4:1 to about 1:1. For tadalafil, which is a still more potent phosphodiesterase inhibitor, the daily dose when co-administered in combination with topiramate according to the method of the invention is in the range of about 36:1 to about 4:1, typically in the range of about 24:1 to about 6:1.

The additional active agent may also be an endothelin receptor antagonist, e.g., bosentan, sitaxsentan, or ambrisentan, with bosentan preferred.

Combination therapy involving a carbonic anhydrase inhibitor and either avanafil or bosentan will generally involve administration of a single dosage form that contains in the range of about 50 mg to about 400 mg topiramate, optimally about 50 mg to about 150 mg topiramate, in sustained release form, and avanafil or bosentan, also preferably in sustained release form. When the additional active agent is avanafil, the amount in the dosage form will generally be such that the weight ratio of topiramate to avanafil provided will be in the range of about 3:1 to about 1:3, preferably about 2:1 to about 1:2, as noted above. With bosentan, the preferred weight ratio of topiramate to bosentan is in the range of about 0.5:1 to about 2:1.

In the method of the invention, the carbonic anhydrase inhibitor is administered to a person suffering from pulmonary hypertension, either primary pulmonary hypertension or secondary pulmonary hypertension. The carbonic anhydrase inhibitor is administered alone or in combination with one or more additional active agents, within the context of a dosing regiment as described above. It has also been found that the carbonic anhydrase inhibitor alleviates or otherwise treats certain causes of pulmonary hypertension, primarily secondary pulmonary hypertension, such as sleep apnea and chronic obstructive pulmonary disease. It has additionally been found that administration of a carbonic anhydrase inhibitor according to the present invention improves the patient's cardiac index (or cardiac output). Further, it has been found that administration of a carbonic anhydrase inhibitor alleviates or otherwise treats certain adverse physiological conditions in addition to pulmonary hypertension, conditions that are often present in patients afflicted with pulmonary hypertension, usually, but not necessarily, with secondary pulmonary hypertension. One such condition is congestive heart failure. Accordingly, the invention further encompasses methods of treating congestive heart failure, sleep apnea, and chronic obstructive pulmonary disease using a carbonic anhydrase inhibitor, optionally in combination with one or more additional active agents, at doses and in formulations as described above.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLE 1

A 26 year-old female with obesity and elevated lipids exhibited a heart murmur, shortness of breath out of proportion to her weight and age, low blood pressure, and leg edema. She underwent an echocardiogram, which showed mitral regurgitation of 1-2+ and mild elevation in pulmonary artery pressure of 36 mm Hg. She was 66" tall, weight 282 lbs, BMI 46, initial BP 118/80. She had 2+ edema of both ankles, clear lungs, and a systolic murmur along the left sternal border, grade II/VI.

She was started on atorvastatin 10 mg daily as well as bupropion 150 mg daily and topiramate 200 mg daily along with a low fat, low carbohydrate diet and exercise. Two weeks after the start of her weight loss program she reported that her exercise tolerance was markedly improved and previous chest pressure and shortness of breath on exertion were gone. She lost weight continuously on the program and 4 months later had lost 20 lbs. A repeat echocardiogram taken 2 weeks after the start of treatment showed only 1+ mitral regurgitation and normal pulmonary pressures. After six months, the patient temporarily discontinued the medications. Within a few days, even though her weight was the same, her chest pressure and shortness of breath on exertion returned. On resumption of the treatment, the symptoms resolved within a few days.

EXAMPLE 2

The second patient was a 57 year-old female with obesity, hypothyroidism, hypertension, valvular heart disease, elevated cholesterol and depression. Her medications were levothyroxine 50 mcg daily, metoprolol 50 mg daily, venlafaxine 37.5 mg daily, progesterone 100 mg daily, esterified estrogens 1.25 mg daily, and methyltestosterone 2.5 mg daily. She was 63" tall, weight 178 lbs, BMI 32, initial BP 120/78. She had trace edema of both ankles and a systolic murmur of I/VI along the left sternal border. An echocardiogram obtained nine months before obesity treatment because of her heart murmur and edema showed mild MR, moderate TR and pulmonary hypertension with a pressure of 39 mm Hg noted. A comment on the report stated that this was a slight increase in pulmonary pressure compared with an echocardiogram taken seven months earlier.

She was treated with phentermine 15 mg daily and topiramate 200 mg daily along with a low fat, low carbohydrate diet and exercise. Metoprolol was discontinued after four months due to low blood pressure. Eight months after treatment started, her weight was 165 lbs, BP was 122/76, and she had no edema. A repeat echocardiogram 1 month later (nine months on treatment for obesity) showed that the pulmonary artery pressure was 33 mm Hg and the tricuspid regurgitation was now rated as mild. No MR was seen.

EXAMPLE 3

The third patient was a 62 year-old female with obesity, hypertension, elevated cholesterol, heart murmur and dyspnea on exertion. Her medications were atorvastatin 10mg daily, captopril 12.5 mg daily, trazodone 50 mg daily, spironolactone 50 mg daily, and bupropion 150 mg daily. She was 64" tall, weight 319 lbs, BMI 55, initial BP 148/76. She had a systolic murmur of I/VI loudest along the left sternal border. An echocardiogram showed mild tricuspid regurgitation, normal LV size and function with probable mild pulmonary hypertension.

She was treated with phentermine 15 mg daily and topiramate 200 mg daily along with a low fat, low carbohydrate diet and exercise. She was instructed to stop both the spironolactone and captopril since this weight loss treatment results in marked lowering of blood pressure in most patients. Three weeks later, before significant weight loss had occurred, a repeat echocardiogram showed no findings of pulmonary hypertension. Blood pressure one week later was 140/86 and weight 317 lbs.

EXAMPLE 4

The fourth patient was a 56 year-old female with obesity, sleep apnea on CPAP, known pulmonary hypertension with PA pressure estimated at 76 mm Hg by echocardiogram, valvular heart disease (mild-moderate tricuspid and mitral regurgitation), depression and hypertension. She smoked just under half pack of cigarettes per day and was a CO2 retainer by ABG's with a PCO2 of 54 mm Hg on room air. She was short of breath with minimal exertion. Her baseline medications were furosemide 80 mg daily, potassium chloride 20 mEq daily, lisinopril 10 mg daily, carvedilol 25 mg BID, escitalopram 10 mg daily, alprazolam 0.5 mg TID, and nightly oxygen. She was 68" tall, weight 284 lbs, BMI 43½, initial BP 122/76. She had 1+ edema of both lower legs and was short of breath on exertion.

She was treated with aspirin 81 mg coated daily, bupropion 300 mg daily, topiramate 100 mg daily, phentermine 5 mg daily, along with a low fat, low carbohydrate diet and light exercise. By the first 4 weeks of follow-up, she had lost 17 lbs and was breathing much better. Four months into the treatment she was clinically markedly improved and able to exercise normally without shortness of breath. She was still smoking cigarettes occasionally. She had lost 38 lbs. Her blood pressure was 110/70 on only lisinopril 10 mg daily. Furosemide and carvedilol had been gradually discontinued due to improved edema, blood pressure, and breathing. An echocardiogram performed at three months into the program was mostly unchanged from her prior echocardiogram except that the pulmonary artery pressure was reported as normal. This change was consistent with her clinical picture.

EXAMPLE 5

The fifth patient was a 70 year-old female with obesity, diabetes, hypertension, hypothyroidism, elevated cholesterol, COPD, and pulmonary hypertension. An echocardiogram 2 years previously showed mild LVH, mild-moderate tricuspid regurgitation, mild RVH, and elevated pulmonary artery pressure of 45-50 mm Hg. She had stopped smoking 1PPD about 10 years previously. Her baseline medications were verapamil 240 mg daily, losartan-HCTZ 50-12.5 daily, levothyroxine 0.125 mg daily, Pulmicort 200 mg 2 puffs twice daily, Foradil powder 12 mg twice daily, metformin 500 mg twice daily, atorvastatin 10 mg daily, fluticasone nasal spray 50 mcg 2 puffs daily and vitamins. She was short of breath with minimal exertion. She was 67" tall, weight 228 lbs, BMI 36, initial BP 138/70.

She was treated with phentermine 15 mg daily and topiramate 100 mg daily. Three years into treatment, her fasting glucose is 106 off metformin compared with 114 on metformin at baseline, her blood pressure is 115/60 on valsartan 80 mg daily and diltiazem CD 120 mg daily (changed from verapamil because of constipation). Her weight has been stable for six months in the low 180's. A follow-up echocardiogram 30 months into treatment showed normal pulmonary pressures. She was also symptomatically much better and exercising more without shortness of breath.

These five patients showed a surprising improvement in pulmonary hypertension, with marked improvement in symptoms in two patients even before significant time had elapsed, and symptomatic improvement in all patients. In addition to treatment with topiramate, a carbonic anhydrase inhibitor, these patients were also subject to a low fat, low carbohydrate diet and weight loss program that typically resulted in mild diuresis and lower blood pressures. However, the improvement in pulmonary pressures appeared to be independent of weight loss in these patients.

EXAMPLE 6

The procedure of Example 1 is repeated with a patient exhibiting similar symptoms with respect to pulmonary hypertension, except that 25 mg zonisamide is substituted for the topiramate. Substantially the same results are expected.

EXAMPLE 7

The procedure of Example 1 is repeated with a patient exhibiting similar symptoms with respect to pulmonary hypertension, except that 50 mg zonisamide is substituted for the topiramate. Substantially the same results are expected.

EXAMPLE 8

The procedure of Example 1 is repeated with a patient exhibiting similar symptoms with respect to pulmonary hypertension, except that 100 mg zonisamide is substituted for the topiramate. Substantially the same results are expected.

EXAMPLE 9

The procedure of Example 1 is repeated with a patient exhibiting similar symptoms with respect to pulmonary hypertension, except that 100 mg acetazolamide is substituted for the topiramate. Substantially the same results are expected.

EXAMPLE 10

The procedure of Example 1 is repeated with a patient exhibiting similar symptoms with respect to pulmonary hypertension, except that 250 mg acetazolamide is substituted for the topiramate. Substantially the same results are expected.

EXAMPLE 11

The procedure of Example 1 is repeated with a patient exhibiting similar symptoms with respect to pulmonary hypertension, except that 500 mg acetazolamide is substituted for the topiramate. Substantially the same results are expected.

EXAMPLES 12-17

The procedures of Examples 2 through 5 are repeated with patients exhibiting similar symptoms with respect to pulmonary hypertension, except that the following are substituted for the amount of topiramate given: 25 mg, 50 mg, and 100 mg zonisamide; and 100 mg, 250 mg, and 500 mg acetazolamide. Substantially the same results are expected.

EXAMPLE 18

Sustained release dosages in the form of gelatin capsules were prepared with a target dose of 15 mg phentermine and 100 mg topiramate per capsule. Phentermine beads were prepared using 20/25 mesh sugar spheres NF and a drug layering solution containing components selected from phentermine, METHOCEL® E5 (hypromellose, produced by The Dow Chemical Company), and water. Topiramate beads were prepared using a spheronized core, a CR coating, and an enteric coating. The spheronized core contained components selected from topiramate, AVICEL® PH102 (microcrystalline cellulose, supplied by FMC BioPolymer), and METHOCEL® A15LV (methylcellulose, produced by The Dow Chemical Company). The CR coating solution contained components selected from EUDRAGIT® RSPO (less permeable, amino methacrylate copolymer, supplied by Degussa Pharma Polymers, Germany), EUDRAGIT° RLPO (more permeable, amino methacrylate copolymer, supplied by Degussa Pharma Polymers, Germany), glycerol monostearate, isopropyl alcohol, and acetone. The enteric coating solution contained components selected from EUDRAGIT® S100 (copolymer of methacrylic acid and methyl methacrylate, supplied by Degussa Pharma Polymers, Germany), glycerol monostearate, isopropyl alcohol, and acetone. Weight percentages (theoretical—not measured) for the final compositions are summarized in Tables 1-3.

TABLE 1

Formulation Summary - capsules containing phentermine beads and topiramate beads

| Final composition, phentermine beads[1] | | Final composition, topiramate beads[2] | |
|---|---|---|---|
| Material | Percent w/w | Material | Percent w/w |
| Phentermine | 7.63 | Topiramate | 31.89 |
| METHOCEL ® E5 | 7.63 | AVICEL ® PH102 | 45.04 |
| 20/25 Sugar Sphere, NF | 84.75 | METHOCEL ® A15LV | 2.79 |
| Total | 100.00 | EUDRAGIT ® RSPO | 0.00 |
| | | EUDRAGIT ® RLPO | 9.28 |
| | | Glycerol Monostearate | 0.29 |
| | | EUDRAGIT ® S100 | 10.39 |
| | | Glycerol Monostearate | 0.32 |
| | | Total | 100.00 |

[1]Target fill weight = 230.7 mg;
[2]Target fill weight = 313.6 mg.

TABLE 2

Formulation Summary - capsules containing phentermine beads and topiramate beads

| Final composition, phentermine beads[1] | | Final composition, topiramate beads[2] | |
|---|---|---|---|
| Material | Percent w/w | Material | Percent w/w |
| Phentermine | 7.63 | Topiramate | 31.89 |
| METHOCEL ® E5 | 7.63 | AVICEL ® PH102 | 45.04 |
| 20/25 Sugar Sphere, NF | 84.75 | METHOCEL ® A15LV | 2.79 |
| Total | 100.00 | EUDRAGIT ® RSPO | 4.64 |
| | | EUDRAGIT ® RLPO | 4.64 |
| | | Glycerol Monostearate | 0.29 |
| | | EUDRAGIT ® S100 | 10.39 |
| | | Glycerol Monostearate | 0.32 |
| | | Total | 100.00 |

[1]Target fill weight = 230.7 mg;
[2]Target fill weight = 313.6 mg.

TABLE 3

Formulation Summary - capsules containing phentermine beads and topiramate beads

| Final composition, phentermine beads[1] | | Final composition, topiramate beads[2] | |
| --- | --- | --- | --- |
| Material | Percent w/w | Material | Percent w/w |
| Phentermine | 7.63 | Topiramate | 31.89 |
| METHOCEL ® E5 | 7.63 | AVICEL ® PH102 | 45.04 |
| 20/25 Sugar Sphere, NF | 84.75 | METHOCEL ® A15LV | 2.79 |
| Total | 100.00 | EUDRAGIT ®RSPO | 6.50 |
| | | EUDRAGIT ® RLPO | 2.78 |
| | | Glycerol Monostearate | 0.29 |
| | | EUDRAGIT ® S100 | 10.39 |
| | | Glycerol Monostearate | 0.32 |
| | | Total | 100.00 |

[1]Target fill weight = 230.7 mg;
[2]Target fill weight = 313.6 mg.

EXAMPLE 19

Dosages in the form of gelatin capsules were prepared with a target dose of 100 mg topiramate per capsule. Topiramate beads were prepared using a spheronized core, an optional CR coating, and an optional enteric coating. The spheronized core contained components selected from topiramate, AVICEL® PH102, and METHOCEL® A15LV. The CR coating solution contained components selected from ethylcellulose (Ethocel Premium Standard 10), Povidone K-30, ethanol (absolute SD3A), EUDRAGIT® RLPO (more permeable), glycerol monostearate, isopropyl alcohol, and acetone. The enteric coating solution contained components selected from EUDRAGIT® S100, EUDRAGIT® L100-55, glycerol monostearate, isopropyl alcohol, and acetone. Weight percentages (theoretical—not measured) for the final compositions are summarized in Tables 4-8. Table 4 describes capsules containing spheronized topiramate beads without a CR coating and without an enteric coating. Tables 5 and 6 describe capsules containing spheronized topiramate beads with a CR coating but without an enteric coating. Tables 7 and 8 describe capsules containing spheronized topiramate beads with an enteric coating but without a CR coating.

TABLE 4

Formulation Summary - capsules containing spheronized topiramate beads
Final composition, topiramate beads[1]

| Material | Percent w/w |
| --- | --- |
| Topiramate | 40.00 |
| AVICEL ® PH102 | 56.50 |
| METHOCEL ® A15LV | 3.50 |
| Total | 100.00 |

[1]Target fill weight = 250.0 mg.

TABLE 5

Formulation Summary - capsules containing spheronized topiramate beads and a CR coating
Final composition, topiramate beads[1]

| Material | Percent w/w |
| --- | --- |
| Topiramate | 36.36 |
| AVICEL ® PH102 | 51.36 |
| METHOCEL ® A15LV | 3.18 |
| Ethylcellulose | 6.36 |
| Povidone K-30 | 2.73 |
| Total | 100.00 |

[1]Target fill weight = 275.0 mg.

TABLE 6

Formulation Summary - capsules containing spheronized topiramate beads and a CR coating
Final composition, topiramate beads[1]

| Material | Percent w/w |
| --- | --- |
| Topiramate | 35.71 |
| AVICEL ® PH102 | 50.45 |
| METHOCEL ® A15LV | 3.13 |
| EUDRAGIT ® RLPO | 10.39 |
| Glycerol Monostearate | 0.32 |
| Total | 100.00 |

[1]Target fill weight = 280.0 mg.

TABLE 7

Formulation Summary - capsules containing spheronized topiramate beads and an enteric coating
Final composition, topiramate beads[1]

| Material | Percent w/w |
| --- | --- |
| Topiramate | 35.71 |
| AVICEL ® PH102 | 50.45 |
| METHOCEL ® A15LV | 3.13 |
| EUDRAGIT ® S100 | 10.39 |
| Glycerol Monostearate | 0.32 |
| Total | 100.00 |

[1]Target fill weight = 280.0 mg.

TABLE 8

Formulation Summary - capsules containing spheronized topiramate beads and an enteric coating
Final composition, topiramate beads[1]

| Material | Percent w/w |
| --- | --- |
| Topiramate | 35.71 |
| AVICEL ® PH102 | 50.45 |
| METHOCEL ® A15LV | 3.13 |
| EUDRAGIT ® L100-55 | 10.39 |
| Glycerol Monostearate | 0.32 |
| Total | 100.00 |

[1]Target fill weight = 280.0 mg.

EXAMPLE 20

Dosages in the form of gelatin capsules were prepared with a target dose of 100 mg topiramate per capsule. Spheronized topiramate beads were prepared using components selected from topiramate, METHOCEL® A15LV, ACDISOL®, AVICEL® PH102, and lactose monohydrate. Weight percentages (theoretical—not measured) for the final compositions are summarized in Tables 9-10. In addition to the dosage forms described in Tables 9-10, a capsule was prepared containing 100 wt % topiramate (target fill weight=100.0 mg).

TABLE 9

Formulation Summary - capsules containing spheronized topiramate beads
Final composition, topiramate beads[1]

| Material | Percent w/w |
|---|---|
| Topiramate | 40.00 |
| AVICEL ® PH102 | 41.00 |
| METHOCEL ® A15LV | 9.00 |
| ACDISOL ® | 10.00 |
| Total | 100.00 |

[1]Target fill weight = 250.0 mg.

TABLE 10

Formulation Summary - capsules containing spheronized topiramate beads
Final composition, topiramate beads[1]

| Material | Percent w/w |
|---|---|
| Topiramate | 40.00 |
| AVICEL ® PH102 | 36.00 |
| METHOCEL ® A15LV | 4.00 |
| Lactose monohydrate | 20.00 |
| Total | 100.00 |

[1]Target fill weight = 250.0 mg.

The invention claimed is:

1. A method for treating secondary pulmonary hypertension in a patient, comprising administering a therapeutically effective dose of topiramate and a therapeutically effective dose of a Type V phosphodiesterase inhibitor to the patient.

2. The method of claim 1, wherein the topiramate additionally treats a cause of the secondary pulmonary hypertension.

3. The method of claim 2, wherein the cause is sleep apnea.

4. The method of claim 2, wherein the cause is chronic obstructive pulmonary disease.

5. The method of claim 1, wherein the topiramate or the Type V phosphodiesterase inhibitor treats an adverse physiological condition in addition to secondary pulmonary hypertension.

6. The method of claim 5, wherein the physiological condition is congestive heart failure.

7. The method of claim 1, wherein the topiramate or the Type V phosphodiesterase inhibitor additionally improve the patient's cardiac index.

8. The method of claim 1, wherein the topiramate is contained in a pharmaceutical formulation that further comprises at least one pharmaceutically acceptable excipient.

9. The method of claim 8, wherein the pharmaceutical formulation is a controlled release dosage form.

10. The method of claim 9, wherein the controlled release dosage form provides for sustained release of the topiramate following administration of the dosage form to the patient.

11. The method of claim 10, wherein the formulation provides for a substantially constant plasma level of the topiramate over a time period in the range of about 4 to 12 hours.

12. The method of claim 1, wherein the topiramate is administered to the patient in an amount in the range of about 10 mg to about 400 mg per day.

13. The method of claim 12, wherein the topiramate is administered to the patient in an amount in the range of about 50 mg to about 250 mg per day.

14. The method of claim 13, wherein the topiramate is administered to the patient in an amount in the range of about 75 mg to about 225 mg per day.

15. The method of claim 1, wherein the Type V phosphodiesterase inhibitor is selected from avanafil, sildenafil, tadalafil, zaprinast, dipyridamole, vardenafil and acid addition salts thereof.

16. The method of claim 15, wherein the Type V phosphodiesterase inhibitor is avanafil.

17. The method of claim 16, wherein the weight ratio of topiramate administered to the avanafil administered is in the range of about 3:1 to about 1:3.

18. The method of claim 17, wherein the weight ratio of topiramate administered to the avanafil administered is in the range of about 2:1 to about 1:2.

19. The method of claim 1, wherein the topiramate and the Type V phosphodiesterase inhibitor are administered at different times of the day.

20. The method of claim 1, wherein the topiramate and the Type V phosphodiesterase inhibitor are administered simultaneously.

21. The method of claim 20, wherein the topiramate and the Type V phosphodiesterase inhibitor are contained in a single formulation.

22. The method of claim 21, wherein the formulation comprises an orally administrable dosage form that, following oral administration of the dosage form to the patient, provides for controlled release of the topiramate, and either immediate release or controlled release of the Type V phosphodiesterase inhibitor.

23. The method of claim 22, wherein the formulation provides for controlled release of the Type V phosphodiesterase inhibitor.

24. The method of claim 23, wherein the formulation provides for sustained release of the Type V phosphodiesterase inhibitor.

25. A method for treating secondary pulmonary hypertension in a patient, comprising administering to the patient: a daily dose of topiramate that is gradually increased, over an extended time period, from an initial daily dosage up to a final daily dosage suitable for continued maintenance therapy, wherein the final daily dosage is in the range of about 10 mg to 400 mg, and a Type V phosphodiesterase inhibitor.

26. The method of claim 25, wherein the final daily dosage is in the range of about 50 mg to about 250 mg.

27. The method of claim 25, wherein the final daily dosage is in the range of about 75 mg to about 225 mg.

28. The method of claim 25, wherein the initial daily dosage is in the range of about 10 mg to about 40 mg.

29. The method of claim 28, wherein the initial daily dosage is in the range of about 15 mg to about 35 mg.

30. The method of claim 25, wherein the extended time period is in the range of about three weeks to about ten weeks.

31. The method of claim 15, wherein the Type V phosphodiesterase inhibitor is tadalafil.

32. The method of claim 31, wherein the weight ratio of topiramate administered to the tadalafil administered is in the range of about 36:1 to about 4:1.

33. The method of claim 32, wherein the weight ratio of topiramate administered to the tadalafil administered is in the range of about 24:1 to about 6:1.

* * * * *